United States Patent [19]

Borenstein et al.

[11] Patent Number: 4,925,841
[45] Date of Patent: May 15, 1990

[54] MANNICH BASES OF SPIROSUCCINIMIDES

[75] Inventors: Michael R. Borenstein, Philadelphia; Peter H. Doukas, Newtown, both of Pa.

[73] Assignee: Temple University of the Commonwealth System of Higher Education, Philadelphia, Pa.

[21] Appl. No.: 211,958

[22] Filed: Jun. 27, 1988

Related U.S. Application Data

[63] Continuation of Ser. No. 757,226, Jul. 22, 1985, abandoned.

[51] Int. Cl.$^5$ .................. C07D 403/14; C07D 31/495
[52] U.S. Cl. ................... 514/235.5; 514/252; 514/253; 514/323; 514/409; 544/70; 544/230; 544/230.8; 546/15; 548/411
[58] Field of Search ............ 544/70, 230; 546/15; 548/411; 514/234, 252, 253, 323, 409

[56] References Cited

U.S. PATENT DOCUMENTS

| | | | |
|---|---|---|---|
| 3,106,552 | 10/1963 | Grogan et al. | 544/70 |
| 3,150,143 | 9/1964 | Grogan et al. | 546/16 |
| 3,200,118 | 8/1965 | Grogan et al. | 544/70 |
| 3,236,862 | 2/1966 | Grogan et al. | 548/408 |
| 3,238,217 | 5/1966 | Grogan et al. | 546/16 |
| 3,256,276 | 6/1966 | Grogan et al. | 544/70 |
| 3,257,398 | 6/1966 | Grogan et al. | 544/70 |
| 3,507,881 | 4/1970 | Sandberg | 548/411 |
| 4,524,206 | 6/1985 | New et al. | 544/230 |

OTHER PUBLICATIONS

"Mannich Bases of Fluorenspiropyrrolidinedione", *Pharmazie* 34, 581–582 (1979) Abou–Gharbia et al.
Bundgaard et al., "Hydrolysis of N–Mannich Bases and its Consequences for the Biological Testing of Such Agents", *Int. J. Pharm.*, 9, 7–16 (1981).
Galvez et al., "Synthesis and Structural Study of Cyclopentane, Indene and Fluorene Spiro–Derivatives", 20, 13–16 (1983), *J. Heterocyclic Chem.*
Abou–Gharbia et al., "Synthesis of Spirofluorenes of Biological Interest", *J. Pharmaceutical Science*, 67, 953–956 (1978).
Tenthorey et al., "New Antirrhythmic Agents. 4. 1'-(Aminoalkyl)-1,2,3,4-Tetrahydronaphthalene-1-Spiro-3'-Pyrrolidine-2',5'-Dione Derivatives", *J. Med. Chem.* 24, 47–53 (1981).
Abou–Gharbia et al., "Synthesis of Tricyclic Arylspiro Compounds as Potential Antileukemic and Anticonvulsant Agents", *Heterocycles*, 12, 637–640 (1979).

Primary Examiner—Mary C. Lee
Assistant Examiner—Catherine S. Kilby Scalzo
Attorney, Agent, or Firm—Seidel, Gonda, Lavorgna & Monaco

[57] ABSTRACT

Mannich bases of spirosuccinimides are provided having anticonvulsant, sedative and antileukemic activity. The compounds have the following formula wherein ring A is a saturated or unsaturated monocyclic or bicyclic carbon ring of at least five carbon atoms:

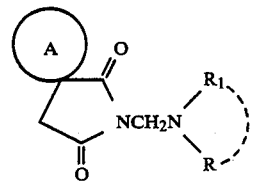

10 Claims, 2 Drawing Sheets

MANNICH BASES OF SPIROSUCCINIMIDES

This is a continuation of co-pending application Ser. No. 757,226 filed on July 22, 1985, now abandoned.

FIELD OF THE INVENTION

The invention relates to Mannich basis of spirosuccinimides having anticonvulsant, sedative and/or antileukemic properties.

BACKGROUND OF THE INVENTION

The ability of spirosuccinimides to alter the excitability of conductive tissues as anticonvulsants, local anesthetics and antiarrhythmics has been reported. Hauck, et al, *J. Med. Chem.*, 10, 611 (1967); Tenthorey, et al, *J. Med. Chem.*, 24, 47 (1981); Alvin, et al, *Anticonvulsants*, (J. A. Vida, Ed.), p. 112, Academic Press (1977).

Mannich bases of spiro-5'-oxazolidine-2,4'-dione are disclosed in *J. Heterocyclic Chem.*, 20, 13 (1983). Mannich bases of spiro[fluorene-9,3'-pyrrolidine]-2,40 ,5'-dione having purported anticonvulsant and antileukemic activity are reported in *J. Pharmaceutical Sci.*, 67, 953 (1978); *Heterocycles*, 12, 637 (1979); and *Pharmazie*, 34, 581 (1979).

Various N-substituted azaspirane-diones are disclosed in the following U.S. Pat. Nos: 3,106,552; 3,150,143; 3,200,118; 3,238,217; 3,256,276; 3,257,398; 3,263,862; 3,507,881. Despite the broad generic teachings of these patents, the present spirosuccinimides are readily distinguished as Mannich bases. They contain only a single carbon atom between the azaspirane-dione nitrogen and the amino nitrogen of the substituent side chain. The presence of the methylene unit gives the present compounds unique chemical properties over compounds which are not Mannich bases.

SUMMARY OF THE INVENTION

Compounds of the formula

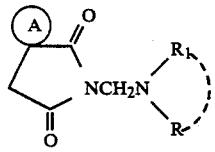

(I)

are provided wherein ring A is selected from the group consisting of saturated and unsaturated monocyclic and bicyclic carbon rings of at least 5 carbon atoms. R and $R_1$ are each selected from the group consisting of lower alkyl, lower alkenyl, cycloalkyl and aryl groups, and when R and $R_1$ are taken together with the nitrogen atom to which they are attached, represent a heterocyclic selected from the group consisting of morpholino, piperidino, pyrrolidino, piperazino and lower alkyl-, lower hydroxyalkyl-, lower haloalkyl-, lower haloalkoxy-, aryl-, haloaryl-, pyridyl-, and arylakyl-substituted derivatives of these heterocyclic groups.

The compounds of the present invention may be taken up in pharmaceutically acceptable carriers, for example, solutions, suspensions, tablets, capsules, ointments, elixers, and injectable compositions and the like. The compositions may be particularly employed as sedatives, and to protect against convulsions.

In a preferred embodiment, ring A comprises a cyclopentyl or cyclohexyl ring. In another preferred embodiment, ring A is an indanyl or indenyl ring.

It is an object of the invention to provide novel, physiologically active compounds and methods for their preparation.

It is an object of the invention to provide novel compounds which are Mannich bases of spirosuccinimides having anticonvulsant, sedative or antileukkemic properties.

It is an object of the invention to provide compositions of these novel compounds in pharmaceutically acceptable carriers for use as anticonvulsants, sedatives and antileukemics.

It is an object of the invention to provide a method of sedation.

Other objects and advantages of the invention will appear hereinafter.

DESCRIPTION OF THE INVENTION

Figure 1:
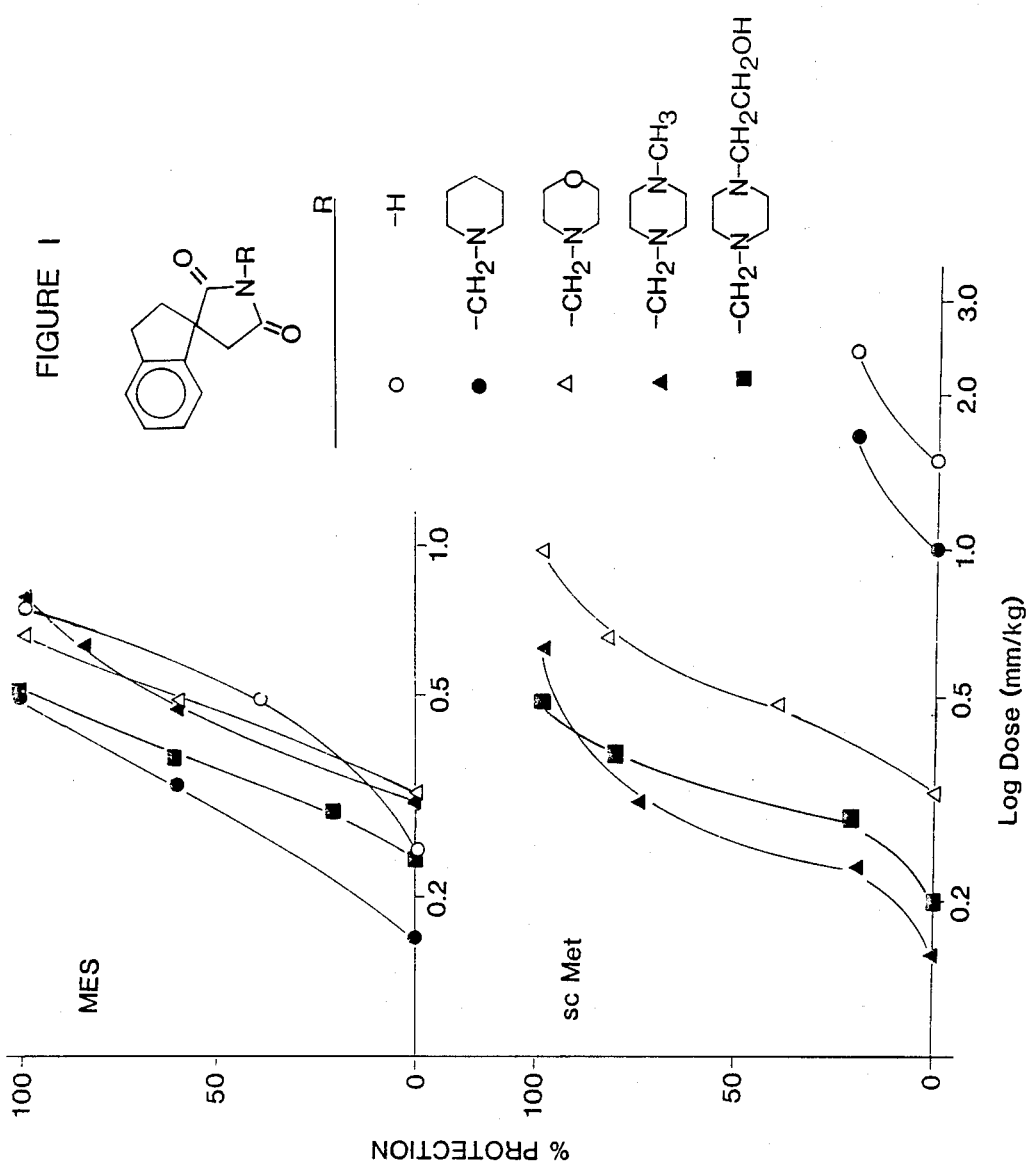
FIG. 1 shows the protection of mice against seizures induced by Maximl Electroshock (MES, 50 mA, 0.2 sec.) and pentylenetetrazole, available as "METRAZOLE", (scMet, 85 mg/kg) by a series of indanylspirosuccinimide Mannich bases. Candidate compounds were administered intraperitoneally thirty minutes prior to seizure challenge to at least 5 animals per dose.

The preferred method for preparing the compounds of the present invention comprises reacting the parent spiroimide with formaldehyde and an appropriate secondary amine under Mannich reaction conditions. The Mannich bases thus prepared have demonstrated anticonvulsant activity in a standard phamacological assay using pentylenetetrazole and/or electroshock as the convulsant agent.

Compounds of formula (I) were prepared as follows. 0.25 moles of the parent ketone were condensed with 0.45 moles of ethyl cyanoacetate in benzene and acetic acid, with ammonium acetate as a catalyst, and refluxed for 18 h under standard Knoevenagel conditions. The condensation product, once isolated and purified, was stirred at room temperature for 4 days in an aqueous ethanolic solution with 2.5 molar equivalents of KCN to yield the dicyano ester. The latter was hydrolyzed and decarboxylated, without prior purification, by refluxing in aqueous HCl/acetic acid for 2 days. Basification with 20% NaOH, heating with activated charcoal, filtration and re-acidification with 5.5M HCl afforded the corresponding diacid. Cyclization of the diacid to its corresponding anhydride was accomplished by refluxing in acetyl chloride for 3 h, removal of the solvent under reduced pressure, and recrystallization of the products from hot benzene. Ammonolysis of the cyclic anhydride in benzene/ether (2.5:1.0) gave the corresponding amido acid which was cyclized in refluxing acetyl chloride, to yield the spiroimide which was recrystallized from hot ethanol/ether. Three molar equivalents of a secondary amine from Table 1 or 2 to one equivalent of imide were mixed thoroughly in a flask contained in an ice bath. To this was added 3 molar equivalents of aqueous formaldehyde with vigorous stirring. The solids thus derived were recrystallized from hot benzene/petroleum ether (1:1).

In a preferred embodiment according to formula (I), ring A is selected from the group of cyclopentyl, cyclohexyl, indanyl and indenyl groups; R and R' form, together with the nitrogen to which they are attached, a heterocyclic ring selected from the group consisting of morpholino, piperidino, N-methyl-piperazino, N-(p-chlorophenyl)piperazino N-hydroxyethylpiperazino and N-(2'-pyridyl)-piperazino; or R and R' are each benzyl groups. Preferred spiroindanylsuccinimides include 1'-methylmorpholino-indan-1-spiro-3'-pyrrolidine-2',5'-dione; 1'-methylpiperidinoindan-1-spiro-3'-pyrrolidine-2',5'-dione; 1'-[methyl-N-(4-chlorophenyl)-piperazino]-indan-1-spiro-3'-pyrrolidine-2',5'-dione; 1'-[methyl-(N-methyl)piperazino]-indan-1-spiro-3'-pyrrolidine-2',5'-dione; 1'-[methyl(N-hydroxyethyl)-piperazino]-indan-1-spiro-3'-pyrrolidine-2',5'-dione; and 1'-[methyl(N-2"pyridyl)piperazino]-indan-3'-pyrrolidine-2',5'-dione. Preferred spirocylopentylsuccinimides include N-methyl-morpholino-2-azaspiro[4.4]nonane-1,3-dione; N-methyl-(N-methyl)piperazino-2-azaspiro[4.4]-nonane-1,3-dione; and N-methyl(N-phenyl)-piperazino-2-azaspiro[4.4]-nonane-1,3-dione.

The physical and spectral properties of nine compounds prepared according to the above procedure from the parent ketones indanone and cyclopentanone are set forth in Tables 1 and 2, respectively. All compounds had correct mass spectral and elemental analyses.

TABLE 1

Spiroindanylsuccinimides

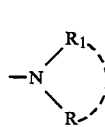

| Example # | Secondary Amine | −N⟨R₁/R'⟩ | mp °C. | Yield | Spectral Data[1] |
|---|---|---|---|---|---|
| 1 | morpholine |  | 103 | 58% | 2.1–3.0(m,5H), 3.2 (s,2H), 7.1–7.5 (m,4H) |
| 2 | piperidine | 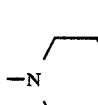 | 80–82 | 66% | 1.1–1.8 (brs,6H), 2.0–3.5(m,10H), 4.5(s,2H), 7.1–7.5 (m,4H) |
| 3 | N-(p-chloro-phenyl)-piperazine | 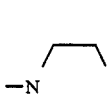 | 185–187 | 91% | 2.1–3.3(m,14H), 4.6(s,2H), 6.7–7.5 (m,8H) |
| 4 | dibenzylamine | −N(CH₂−C₆H₅)₂ | 115–117 | 96% | 2.3–3.3(m,6H), 3.8(s,4H), 4.6 (s,2H) 7.1–7.5 (m,14H) |
| 5 | N-methyl-piperazine | 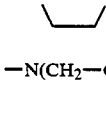 | 113–114 | 67% | 2.1–3.3(m,4H), 2.3 (s,3H) 2.4–2.80 (m,8H) 3.0(s,2H), 4.53(s,2H) 7.1–7.5 (m,4H) |
| 6 | N-hydroxy-ethylpiperazine | 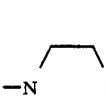 | 109–111 | 40% | 2.2–3.4(m,17H), 3.4–3.9(t,2H),4.6 (s,2H),6.9–7.8 (m,4H) |
| 7 | N-2"pyridyl)-piperazine | 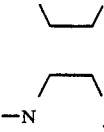 | 120–122 | 50% | 2.0–3.3(m,10H); 3.4–3.9(m,4H); 4.6(s,2H); 6.5–6.9 (m,2H); 6.9–7.8 (m,5H); 8.1–8.4(m,1H) |

$^1$HNMR Chemical shifts (ppm) in CDCl₃ with TMS internal standard.

TABLE 2
Spirocyclopentylsuccinimides

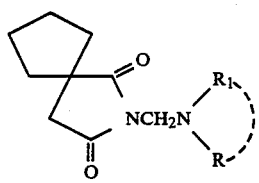

| Example # | Secondary Amine | −N⟨R₁/R⟩ | mp °C. | Yield | Spectral Data[1] |
|---|---|---|---|---|---|
| 8 | morpholine | −N⟨ ⟩O | 69–71 | 55% | 1.5–2.0 (m,8H), 2.5–1.8 (m,6H), 3.5–3.9 (q,4H), 4.5 (s,2H) |
| 9 | N-methyl-piperazine | −N⟨ ⟩N−CH₃ | 110–112 | 82% | 1.3–3.6(m,8H), 2.5(s,2H) |
| 10 | N-phenyl-piperazine | −N⟨ ⟩N−C₆H₅ | 117–119 | 71% | 1.3–2.3 (m,8H), 2.4–2.9 (m,6H), 2.9–3.4 (m,4H), 4.3 (s,2H), 6.6–7.5 (m,5H) |

The anticonvulsant activity of these compounds was determined according to the standard pharmacological assay of Swinyard, et al, *J. Pharmacol. Exp. Ther.*, 106, 319 (1952), using pentylenetetrazole and/or electroshock.

Briefly, a spirosuccinimide according to the present invention was administered to mice intraperitoneally as a suspension in 0.5% methyl cellulose in volumes of 0.09–0.3 ml. One half hour later, 85 mg/kg pentylenetetrazole was administered subutaneously. The results are scored in Table 3 wherein S means sedation, A means ataxia, and LRR means loss of righting reflex.

TABLE 3
Protection Against Penteylenetetrazole In Mice

| Cpd | mg/kg | # of Animals/dose | Observations | % Protection |
|---|---|---|---|---|
| Spiroindanylsuccinimide | 300 | 5 | S | — |
|  | 500 | 5 | S | 20 |
| Example #1 | 100 | 5 | S | — |
|  | 150 | 5 | S | 40 |
|  | 200 | 11 | S,A | 82 |
|  | 300 | 5 | S,A,LRR | 100 |
| Example #2 | 50 | 5 | S | — |
|  | 150 | 5 | S | — |
|  | 300 | 12 | S | — |
|  | 475 | 5 | S,LRR | — |
|  | 500 | 5 | S,LRR | 20 |
| Example #3 | 300 | 5 | S | — |
| Example #4 | 400 | 5 | S | — |
|  | 800 | 5 | S | — |
| Example #5 | 50 | 5 | S | — |
|  | 75 | 5 | S | 20 |
|  | 100 | 5 | S | 75 |
|  | 200 | 5 | S | 100 |
| Example #6 | 70 | 5 | S | 0 |
|  | 100 | 5 | S | 20 |
|  | 135 | 5 | S | 80 |
|  | 170 | 5 | S | 100 |
| Example #7 | — | — | — | — |
| Example #8 | — | — | — | — |
| Example #9 | 500 | 5 | S | — |

Anticonvulsant activity against electroshock was established as follows. One half hour after intraperitoneal administration of the test compound in 0.5% methyl cellulose in volumes of 0.09–0.03 ml, mice were subjected to a maximal electroshock of magnitude 50 ma/0.2 sec. Sedation, ataxia and loss of righting reflex were scored as before. The results appear in Table 4.

TABLE 4
Protection Against Maximal Electroshock In Mice

| Cpd | mg/kg | # of Animals/dose | Observations | % Protection |
|---|---|---|---|---|
| Spiroindanylsuccinimide | 50 | 5 | S | 0 |
|  | 100 | 5 | S | 40 |
|  | 150 | 5 | S,A | 100 |
| Example #1 | 100 | 5 | — | 0 |
|  | 150 | 5 | S | 60 |
|  | 200 | 5 | S,A | 100 |
| Example #2 | 50 | 5 | S | 0 |
|  | 100 | 5 | S | 60 |
|  | 150 | 5 | S,A | 100 |
| Example #5 | 100 | 5 | S | 0 |
|  | 150 | 5 | S,A | 60 |
|  | 200 | 5 | S,A | 80 |
|  | 250 | 5 | S,A | 100 |
| Example #6 | 85 | 5 | S | 0 |
|  | 100 | 5 | S | 20 |
|  | 135 | 5 | S | 60 |
|  | 170 | 5 | S | 100 |

Some degree of sedation was observed in all of the compounds tested, although this did not parallel protection against seizures. Although the spirocyclopentylsuccinimide Mannich base of Example 8 failed to provide protection against seizures in the pentylenetetrazole screen, several of the spiroindanylsuccinimide Mannich bases showed protective effects in both pentylenetetrazole and maximum electroshock assays.

The dose-effect curves for spiroindanyl derivatives (FIG. 1) in the two assay systems reveal the following:

In the maximum electroshock screen, the order of the activity was as follows:

Piperidine > Hydroxyethylpiperazine > Morpholine = N-Methylpiperazine > Parent Imide ED$_{50}$ Range (5 Cpds): 0.3 mM/Kg to 0.5 mM/Kg The order of activity in the pentylenetetrazole screen was:

N-Methylpiperazine > Hydroxyethylpiperazine = Morpholine > > Piperidine > Parent Imide ED$_{50}$ Range (3 Cpds): 0.27 mM/Kg to 0.55 mM/Kg It appears that the chemically-induced seizures are more sensitive to structural changes than seizures induced by electroshock. The piperidinyl and parent imides are most selective for MES-seizures, the N-Methylpiperazinyl imide is most selective for pentylenetetrazol seizures. The N-morpholino and N-Hydroxyethylpiperazinyl imides appear to be equiactive in both assays.

Figure 2:
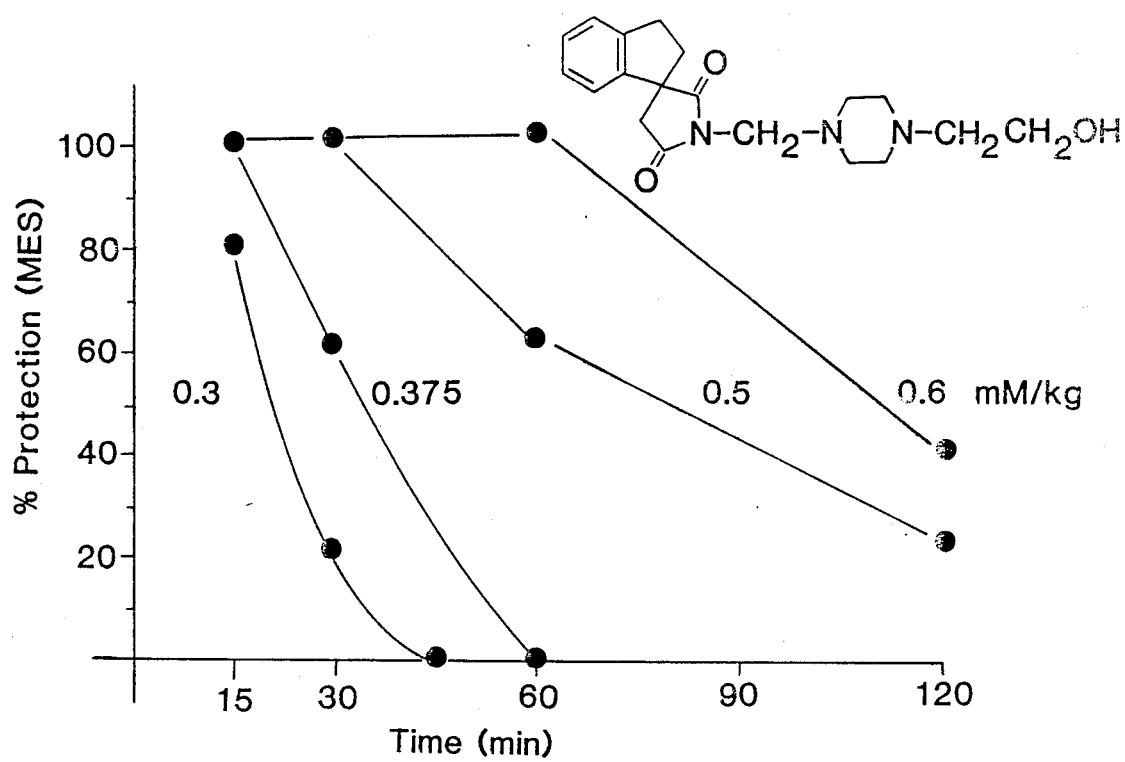
FIG. 2 shows the protection of mice against MES as a function of dose and time for a representative compound of the present invention, 1'-[methyl(N-hydroxyethyl)piperazino]-indan-1-spiro-3'-pyrrolidine-2',5'-dione.

Various doses (0.3; 0.375; 0.5; 0.6 mM/Kg) of the hydroxyethylpiperazinyl Mannich base of indanyl-1-spirosuccinimide (Example #6) were injected (i.p.) into four groups of mice. Thereafter the mice were challenged by electroshock at various time intervals (15, 30, 60, and 120 minutes). The protective efficacy is presented in FIG. 2. Each data point represents n=5 mice/dose/time interval. The compound appears to rapidly penetrate the central nervous system as evidenced by the protection afforded 15 minutes after administration. Increased doses result in prolonged protection; a doubling of the dose leads to a tenfold increase in protective half-life.

The present invention may be embodied in other specific forms without departing from the spirit or essential attributes thereof and, accordingly, reference should be made to the appended claims, rather than to the foregoing specification, as indicating the scope of the invention.

We claim:
1. A compound of the formula

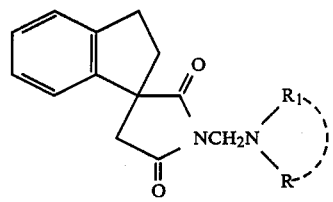

wherein R and R$_1$ taken together with the nitrogen atom to which they are attached, represent a heterocyclic group selected from the group consisting of morpholino, piperidino, pyrrolidino, piperazino, and lower alkyl-, lower hydroxyalkyl-, lower haloalkyl-, lower haloalkoxy-, lower alkoxy-, aryl-, haloaryl-, pyridyl- and arylalkyl-substituted derivatives of said heterocyclic groups.

2. A compound according to claim 1 wherein R and R$_1$ form, together with the nitrogen to which they are attached, a heterocyclic ring selected from the group consisting of morpholino, piperidino, N-methylpiperazino, N-(p-chlorophenyl)piperazino, N-hydroxyethylpiperazino and N-(2″-pyridyl)piperazino.

3. An anticonvulsant composition which comprises a compound of claim 1 and a pharmaceutically acceptable carrier.

4. An anticonvulsant composition which comprises a compound of claim 2 and a pharmaceutically acceptable carrier.

5. 1′-methylmorpholino-indan-1-spiro-3′-pyrrolidine-2′,5′-dione, being a compound of claim 1.

6. 1′-methylpiperidino-indan-1-spiro-3′-pyrrolidine-2′,5′-dione, being a compound of claim 1.

7. 1′-[methyl-N-(4-chlorophenyl)piperazino]-indan-1-spiro-3′-pyrrolidine-2′,5′-dione, being a compound according to claim 1.

8. 1′-[methyl-(N-methyl)piperazino]-indan-1-spiro-3′-pyrrolidine-2′,5′-dione, being a compound according to claim 1.

9. 1′-[methyl-(N-hydroxyethyl)piperazino]-indan-1-spiro-3′-pyrrolidine-2′,5′-dione, being a compound according to claim 1.

10. 1′-[methyl-(N-2″pyridyl)piperazino]-indan-1-spiro-3′-pyrrolidine-2′,5′-dione, being a compound according to claim 1.

* * * * *

UNITED STATES PATENT AND TRADEMARK OFFICE
CERTIFICATE OF CORRECTION

PATENT NO. : 4,925,841

DATED : May 15, 1990

INVENTOR(S) : Michael R. Borenstein et al.

It is certified that error appears in the above-identified patent and that said Letters Patent is hereby corrected as shown below:

Column 1, line 22, change "2,40 ,5'-" to --2',5'--.
Column 2, line 9, change "antileukkemic" to --antileukemic--; line 22, change "Maximl" to --Maximal--. Column 3, line 13, change "1'-methylpiperidinoindan" to --1'-methylpiperidino-indan--. Column 5, line 39, change "inraperitoneally" to --intraperitoneally--; line 42, change "subutaneously" to --subcutaneously--.

Signed and Sealed this

Sixth Day of August, 1991

Attest:

HARRY F. MANBECK, JR.

Attesting Officer

Commissioner of Patents and Trademarks